(12) United States Patent
Zhao et al.

(10) Patent No.: US 7,658,121 B2
(45) Date of Patent: Feb. 9, 2010

(54) FLOW CYTOMETRIC APPARATUS AND METHOD

(75) Inventors: Bingqiang Zhao, Shenzhen (CN); Quan Gan, Shenzhen (CN); Chengwei Sun, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 193 days.

(21) Appl. No.: 11/986,166

(22) Filed: Nov. 20, 2007

(65) Prior Publication Data

US 2008/0250876 A1    Oct. 16, 2008

(30) Foreign Application Priority Data

Apr. 16, 2007    (CN) .................. 2007 1 0074105

(51) Int. Cl.
*G01N 35/10* (2006.01)
(52) U.S. Cl. .................. 73/864.22
(58) Field of Classification Search .............. 73/864.22
See application file for complete search history.

(56) References Cited

U.S. PATENT DOCUMENTS

| | | | | |
|---|---|---|---|---|
| 5,134,445 | A | * | 7/1992 | Toge ............... 356/336 |
| 5,182,617 | A | * | 1/1993 | Yoneyama et al. ....... 356/440 |
| 5,895,764 | A | | 4/1999 | Sklar et al. |

FOREIGN PATENT DOCUMENTS

| | | |
|---|---|---|
| CN | 1204267 C | 6/2005 |
| CN | 01000306 A | 7/2007 |
| EP | 1348943 A | 10/2003 |
| JP | 6034518 A | 2/1994 |
| JP | 6194299 A | 7/1994 |
| JP | 2001296233 A * | 10/2001 |

OTHER PUBLICATIONS

Chinese Search Report dated Aug. 8, 2007 for China patent application No. 200710074105.1.
Yi, Zhang, "The Introduction to the Flow Cytometer", China Academic Journal electronic Publishing House, Aug. 2005, p. 25-26.
"Principle of Flow Cytometry", China Academic Journal Electronic Publishing House, Article No. 1004-2113 (2002) 03-0203-0205.
English translation of abstracts for EP1348943A, JP6034518A, JP6194299A, CN1204267C, CN101000306A and two articles reference above.

* cited by examiner

*Primary Examiner*—Hezron Williams
*Assistant Examiner*—Tamiko D Bellamy
(74) *Attorney, Agent, or Firm*—Vista IP Law Group, LLP.

(57) ABSTRACT

The present invention discloses a flow cytometric apparatus comprising a flow chamber to be passed through by a sample in a row in sequence, a sample storage means for metering and storing the sample, a sample syringe for driving the sample into the flow chamber, a syringe-type injection-suction means comprising a sheath liquid syringe and a liquid-path switching means connected with it, and a control unit for controlling the operations of the sample syringe and the syringe-type the injection-suction means. In a sample charging stage, the injection-suction means feeds the sample into the sample storage means so that the sample is temporarily stored in it in a ready-to-use state, and in a sheath-liquid injection stage, the injection-suction means feeds the sheath liquid into the flow chamber to form a sheath flow. A flow cytometric method performed by the flow cytometric apparatus is also disclosed.

20 Claims, 5 Drawing Sheets

Fig. 1

(prior art)

Fig. 2

(prior art)

FLOW CYTOMETRIC APPARATUS AND METHOD

CROSS-REFERENCE TO RELATED APPLICATION

This application claims the benefit of Chinese Patent Application No. 200710074105.1, filed Apr. 16, 2007, the disclosure of which is hereby incorporated herein by reference in its entirety.

TECHNICAL FIELD

The present invention relates to a flow cytometric apparatus and a flow cytometric method.

BACKGROUND ART

Such flow cytometric apparatus and methods are applicable in, among others, the fields of blood cell detection and particle analysis, for detecting or measuring the number and size of cells or particles.

Figure 1:
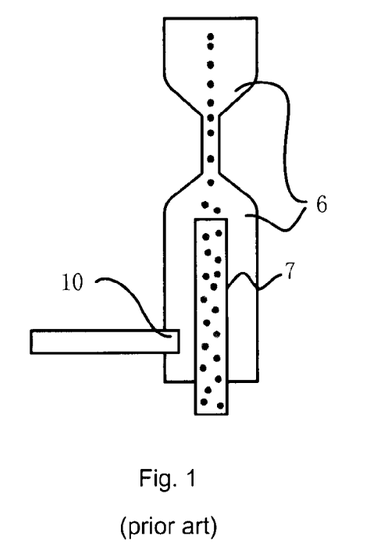
FIG. 1 is a diagrammatic view of flow cytometry.

In the fields of blood cell detection and particle analysis, the cells or particles to be detected generally flows through a small hole, and, by means of an optical or electrical detection procedure, the number and size information and the internal characteristics of the cells or particles can be obtained by analysis. In order that the cells or particles may pass through the small hole in a more regularly path, a clean liquid (sheath liquid) may be introduced to cover the sample which is under detection and passing through the small hole. In this way, the cells or particles can pass through the middle part of the small hole. As shown in FIG. 1, the sample particulates injected into a flow chamber 6 by a sample needle 7 are covered by the sheath liquid injected into the flow chamber 6 via a sheath liquid inlet 10, and pass through the small hole of the flow chamber 6 in a row in sequence, thus the detection can be conveniently performed. This process or method is referred as flow cytometry.

Figure 2:
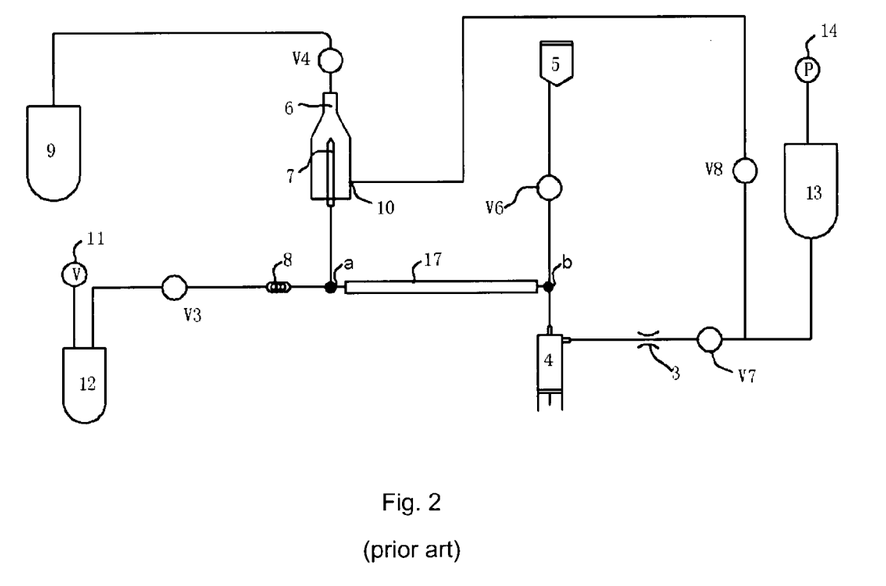
FIG. 2 is a schematic view of the liquid path in a traditional flow cytometric apparatus.

A general apparatus for carrying out flow cytometry is shown in FIG. 2, wherein reference numeral 5 represents a sample pool, the sample to be detected, which has been formed by reaction, being stored in the sample pool; numeral 12 represents a negative pressure pool which is connected with a negative pressure source 11 so that a negative pressure is maintained in the negative pressure pool 12 for drawing the sample from the sample pool 5 into a conveying line; numeral 13 represents a sheath liquid pool which is connected with a positive pressure source 14 so that a positive pressure is maintained in the sheath liquid pool 13 for providing the sheath liquid from the sheath liquid pool 13 to the flow chamber 6 under the driving power of the positive pressure provided from the sheath liquid pool 13; numeral 4 represents a sample injecting syringe, which provides a driving power to inject the sample into the flow chamber 6; numeral 6 represents a flow chamber, through which the sample to be detected is flowing and being detected at the meantime; numeral 7 represents a sample needle, the sample being injected into the flow chamber 6 through the sample needle 7; numeral 9 represents a waste pool, the sheath liquid and the sample, after passing through the small hole of the flow chamber 6, being discharged through a waste discharge port of the flow chamber to waste pool 9; numeral 17 represents a sample charging tube; and finally, numeral and 3 represents a flow restrictor.

The process carried out by the above apparatus will be described now. First, a first normally-closed two-way valve V3 and a fourth normally-closed two-way valve V6 are opened, the sample prepared by reaction and brought into the sample pool 5 under the effect of the negative pressure of negative pressure pool 12 is drawn into a conveying line between the fourth two-way valve V6 and a storage tube 8 (which conveying line including the sample charging tube 17). Then the first two-way valve V3 and the fourth two-way valve V6 are closed, and a third normally-closed two-way valve V4 and a sixth normally-closed two-way valve V8 are opened, so that the sheath liquid flows through the flow chamber 6 under the effect of the positive pressure of the sheath liquid pool 13. Then the sample syringe 4 pushes the sample forward to feed it into the flow chamber 6. Alternatively, for feeding the sample to the flow chamber 6 more quickly, a fifth normally-closed two-way valve V7 may be opened in a short time period once, so that the sample is pushed forward quickly under the pressure provided by the sheath liquid pool 13. After the flow of the sample comes to a stable state, the detection to it can be initiated.

In the prior art described above, constant pressure sources provide the driving power for driving the sheath liquid and for charging the sample. The constant pressure sources are expensive for comprising two sets of air pressure sources and two sets of pressure regulators. Meanwhile, air conveying lines adopted in the apparatus result in an increased complexity of the system, which prevents the detection equipments adopting such apparatus from being miniaturized. In addition, a blockage in the flow chamber cannot be found out directly. Rather, the blockage in the flow chamber can be only found out indirectly by an abnormal detection result. Thus, there is a certain possibility of making misjudgments, and it is difficult to determine the location of the blockage. In the condition that the driving system with constant pressure sources is substituted by a driving system with a constant flow syringe, when the flow chamber is blocked, the pressure in the liquid conveying system will be increased dramatically. It follows that the fittings of the liquid conveying system disengage in a short time, and biologically dangerous liquid may be splashed out.

SUMMARY OF INVENTION

An object of the present invention is to provide a flow cytometric method and apparatus to overcome at least some of the defects existed in the prior art. The apparatus of the invention is expected to have a simple structure and is cost effective, and the detection equipment adopting such an apparatus is easy to be miniaturized.

To achieve the above object, the present invention, in one aspect, provides a flow cytometric apparatus comprising: a flow chamber adapted to be passed through by a sample to be detected in a row in sequence so that the sample can be detected, the flow chamber comprising a sheath liquid inlet for the injection of a sheath liquid and a sample needle for the injection of the sample; a sample storage means for storing the sample to be detected; a sample syringe for driving the sample to be detected into the flow chamber, so as to form a sample flow to be detected; a syringe-type injection-suction means comprising a sheath liquid syringe and a liquid-path switching means connected with it, wherein the liquid-path switching means controllably connects the sheath liquid inlet and the sample storage means for receiving the sheath liquid, and wherein the injection-suction means functions in a manner that, in a sample charging stage, the injection-suction means feeds the sample into the sample storage means so that the sample is temporarily stored in it in a ready-to-use state, and in a sheath-liquid injection stage, the injection-suction means feeds the sheath liquid into the flow chamber to form a sheath flow; and a control unit for controlling the operations of the sample syringe and the syringe-type the injection-suction means.

According to an embodiment of the present invention, preferably, the flow cytometric apparatus of the invention may include one or more of the features listed below.

When the sheath liquid syringe is actuated for suction, the sample is fed into the liquid storage means, or the sheath liquid is drawn into the sheath liquid syringe, and when the sheath liquid syringe is actuated for injection, the sheath liquid is fed into the flow chamber through the sheath liquid inlet to form the sheath flow.

Further, the liquid-path switching means comprises a first three-way valve and a second three-way valve, the first three-way valve having a common end which is connected with the sheath liquid syringe, a normally-closed end which is connected with the sample storage means, and a normally-opened end which is connected with a common end of the second three-way valve, and the second three-way valve having the common end which is connected with the normally-opened end of the first three-way valve, a normally-opened end which is connected for receiving the sheath liquid, and a normally-closed end is connected with the sheath liquid inlet.

Moreover, the flow cytometric apparatus further comprises an overpressure protection means which is connected to and communicated with a conveying line provided between the sheath liquid inlet and the injection-suction means.

Furthermore, the overpressure protection means comprises a pressure sensing means which is connected to and communicated with a conveying line provided between the injection-suction means and the sheath liquid inlet, for monitoring the pressure in the sheath-liquid conveying line, and wherein the pressure sensing means is connected with the control unit, and the control unit compares the pressure level obtained from the pressure sensing means with a predetermined upper limit of normal pressure and sends out a command to stop the operation of a corresponding syringe when the pressure level is determined to be an overpressure.

Furthermore, the pressure sensing means is a pressure sensor.

Furthermore, the overpressure protection means is an overpressure self-release means, the overpressure self-release means having one end connected with a conveying line provided between the sheath liquid inlet and the injection-suction means and another end connected with a waste pool.

Furthermore, the overpressure self-release means is a pressure relieve valve.

Furthermore, the liquid storage means comprises a sample charging tube, a first three-way connection and a second three-way connection, the sample charging tube having one end connected with the sample needle and the injection-suction means via the first three-way connection and another end connected with the sample syringe via the second three-way connection.

Moreover, the flow cytometric apparatus further comprises a storage tube which is connected between the injection-suction means and the first three-way connection.

Moreover, the flow cytometric apparatus further comprises a pressure equalizing means which is connected between the injection-suction means and the sample syringe, wherein, before the sample syringe is actuated for feeding the sample, the sample flows into the flow chamber quickly by the activation of the pressure equalizing means.

Furthermore, the pressure equalizing means comprises a third two-way valve and a flow restrictor, the flow restrictor having one end connected with the sample syringe and another end connected with the injection-suction means via the third two-way valve.

The present invention, in another aspect, provides a flow cytometric method performed by the above described apparatus, which comprises the steps of:

A) sample charging, in which, by means of the injection-suction means, the sample to be detected is fed into the sample storage means so that the sample is temporarily stored in it in a ready-to-use state;

B) injection of the sheath liquid, in which, by means of the injection-suction means, the sheath liquid is injected into the flow chamber to form a stable and smooth sheath flow;

C) injection of sample, in which the sample to be detected, which is stored in the sample storage means, is injected into the flow chamber to form a stable and smooth sample flow to be detected; and D) detection, in which the sample flow passing through the flow chamber is detected.

Preferably, the flow cytometric method of the invention may include one or more of the features listed below.

When the sheath liquid is injected, an overpressure protection means is activated to perform overpressure protection in the sheath-liquid conveying line.

Further, the overpressure protection means is a pressure sensing protection means which monitors the pressure in the sheath-liquid conveying line by a pressure sensing means, and the control unit compares the pressure level obtained from the pressure sensing means with a predetermined upper limit of normal pressure and sends out a command to stop the operation of a corresponding syringe when the pressure level is determined to be an overpressure.

Furthermore, the overpressure protection means is an overpressure self-release means, and when the pressure in the sheath-liquid conveying line is at an overpressure, the overpressure self-release means bypasses the sheath flow around the flow chamber, so that the sheath is drained directly into a waste pool via the flow overpressure self-release means.

Moreover, the flow cytometric method further comprises a step of cleaning of sheath-liquid conveying line after releasing of overpressure, in which, after the operation of the syringe is stopped in an overpressure condition and the overpressure in the flow chamber is released, the parts of the conveying line which have been flowed through by the sample flow are cleaned by a flow of sheath liquid.

Furthermore, the step of cleaning of sheath-liquid conveying line after releasing of overpressure is a back flow cleaning step, in which the washing sheath liquid flows in a direction reverse to that of the sample, so that the sample remained in the conveying line is forced back to the sample pool.

Moreover, the flow cytometric method further comprises a step of cleaning, in which, after detection, the sheath liquid washes the parts of the conveying line which have been flowed through by the sample flow.

Moreover, the flow cytometric method further comprises a step of pressure equalizing, in which, before the sample is injected, a the pressure equalizing means is activated, so that a part of the sample to be detected, which is stored in the sample storage means, is branched out from the sample storage means and is then injected into the flow chamber quickly.

According to the present invention, significant advantages can be obtained over the prior art.

Specifically, the injection-suction means formed by syringes can create both a positive pressure and a negative pressure. Thus the injection of the sheath liquid and the charging of the sample are both driven by the injection-suction means, without using two sets of driving means. As a result, the whole apparatus has a simple structure, and the detection equipment adopting such an apparatus is easy to be miniaturized.

Moreover, a syringe type driving means is adopted, and thus the traditional large and expensive constant pressure sources are omitted, which results in a further miniaturization and cost reduction of the detection equipment.

In the case that the sheath-liquid conveying line is connected with an overpressure protection means, any dangerous can be avoided in the condition that the system is over pressured.

In the case that the sheath-liquid conveying line is connected with a pressure sensing means which reports an abnormal pressure to a control unit in the condition of overpressure, and the control unit sends a command to the fluid conveying unit to release the pressure, system safety can be ensured. Meanwhile, an alarm provided by the pressure sensing means may help to locate the defective point.

In the case that an overpressure self-release means is branched out from the sheath-liquid conveying line, so that in an overpressure state the sheath liquid is bypassed around the flow chamber and is directly discharged into a waste pool, the dangerous caused by overpressure can be avoided automatically and effectively.

When a storage tube for storing excessive sample is provided between the sample storage means and the injection-suction means, the sample storage means can be filled up with the sample to be detected, and meanwhile, the injection-suction means can be prevented from being contaminated by the sample.

In the case that a pressure equalizing means is provided, the sample flow is first pushed into the flow chamber by a part of branched sheath liquid. Thus, the resistance met in the initial sample injection stage of the sample syringe can be lowered down, and a sample flow can be formed quickly.

Since the pressure equalizing means comprises only a two-way valve and a flow restrictor, a simple and cost effective structure can be provided. In the case that the flow restrictor is a flow restricting tube, the sample flow rate can be adjusted by changing the length of the flow restricting tube. In addition, after the sample enters into the flow chamber, the sample syringe is actuated and the two-way valve of the pressure equalizing means is closed, and thus a stable and smooth sample flow is formed.

BRIEF INTRODUCTION TO THE DRAWINGS

The present invention will be described in details with reference to the drawings in which.

DETAILED DESCRIPTION OF THE PREFERRED EMBODIMENTS

First Embodiment of the Invention

A flow cytometric apparatus according to the first embodiment of the invention, as shown in FIG. 1, comprises a dilution liquid (sheath liquid) barrel 1, a sample syringe 4, a sample pool 5, a flow chamber 6, a sample needle 7, a storage tube 8, a waste pool 9, a sheath liquid inlet 10, a pressure sensing means 15, a sample storage means 18, a pressure equalizing means 19, a syringe-type injection-suction means 20, a first normally-closed two-way valve V3, a second normally-closed two-way valve V4, a fourth normally-closed two-way valve V6, and related conveying lines. The sample storage means 18 comprises a first (tee coupling) three-way connection "a", a second three-way connection "b" and a sample charging tube 17. The pressure equalizing means 19 comprises a third normally-closed two-way valve V5 and a flow restrictor 3. The injection-suction means 20 comprises a sheath liquid syringe 2, a first three-way valve V1 and a second three-way valve V2.

Figure 3:
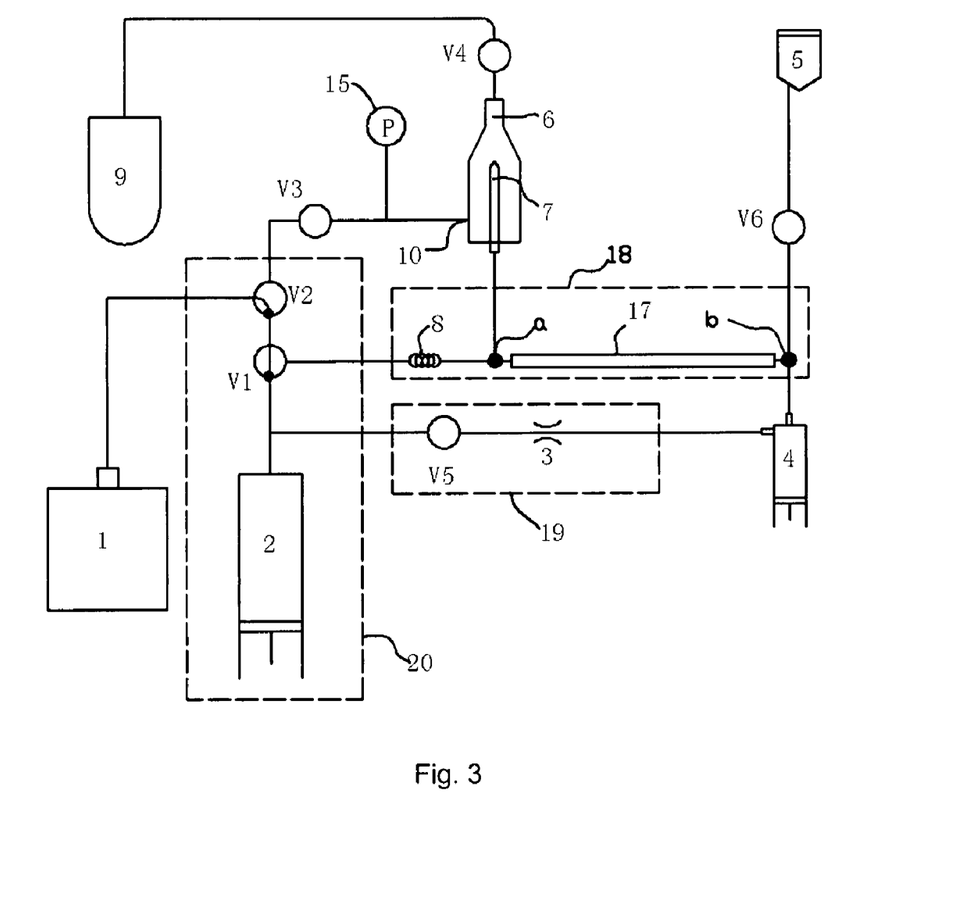
FIG. 3 is a schematic view of the liquid paths in the flow cytometric apparatus according to the first embodiment of the invention in the normal state of the apparatus.

The dilution liquid barrel 1 is designed to store a clean sheath liquid. The sheath liquid syringe 2 is designed to drive the sheath liquid from the dilution liquid barrel 1 to the flow chamber 6, and is also designed to drive the sample flow from the sample pool 5 to the sample charging tube 17 which is connected with an inlet of the sample needle 7 so that the sample is temporarily stored in a ready to use state. The flow restrictor 3 is designed to restrict the flow rate of the sheath liquid in the pressure equalizing means 19. The flow restrictor 3 may be a flow restricting tube. In this case, the flow rate can be adjusted by changing the length of the flow restricting tube. The sample syringe 4 is designed to push forward the sample to be detected which is stored in the sample charging tube 17, so as to feed it into the flow chamber 6. The sample pool 5 is designed to store the sample to be detected which has been prepared by reaction. The sample surrounded by the sheath liquid passes through the flow chamber 6 and is detected in the meantime. The flow chamber 6 has at least three ports, the sample being injected into the flow chamber through one of these ports. This port may be formed by the sample needle 7. That is to say, the sample is injected into the flow chamber 6 through the sample needle 7. The second port of the flow chamber 6 is formed by the sheath liquid inlet 10, through which the sheath liquid flows into the flow chamber 6 to form a sheath flow. The flow chamber 6 has a small hole to be passed through by the sample in a row in sequence. The sheath liquid and the sample, after passing through the small hole of the flow chamber 6, are discharged to the waste pool 9 through a waste discharge port (the third port) of the flow chamber. The storage tube 8 has a certain volume for storing excessively stored sample. By means of the storage tube 8, the sample charging tube 17 can be filled up by the sample, while the sample is prevented from entering into the sheath liquid syringe 2. The pressure sensing means 15 is designed to detect whether the pressure in the sheath-liquid conveying line is over a predetermined level during a sheath-flow forming period. The sample charging tube 17 is capable of metering the sample to be detected. The sample to be detected each time is previously stored in the sample charging tube 17.

The flow cytometric apparatus in the first embodiment of the invention has a liquid path connected in the way discussed below.

Figure 6:
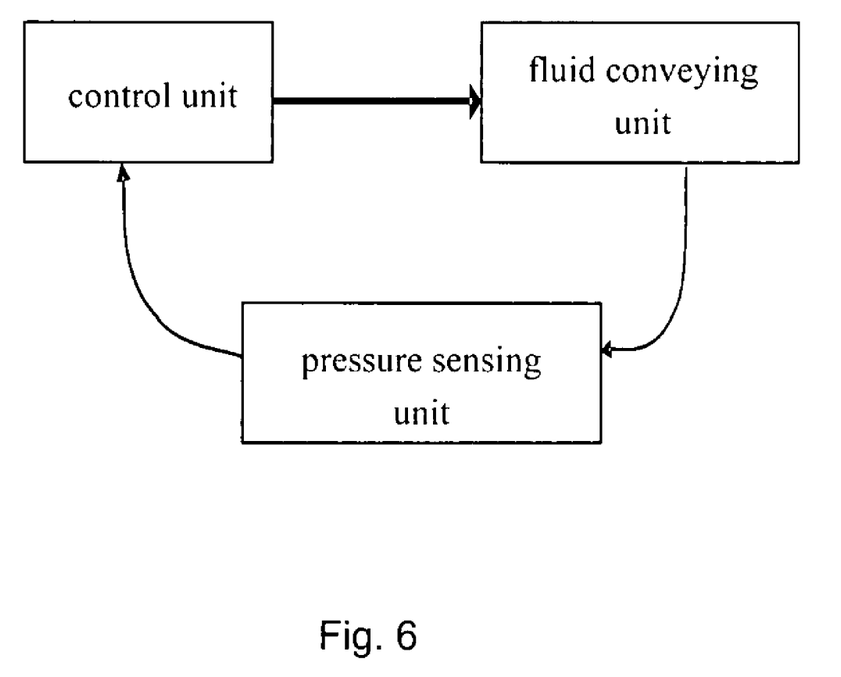
FIG. 6 is a block view showing the control process in an embodiment of the invention.

As shown in FIG. 3, in the first embodiment, the sample storage means 18 comprises the storage tube 8, the sample charging tube 17, the first three-way connection "a" and the second three-way connection "b". The first three-way connection "a" and the second three-way connection "b" each have a port connected with the opposite ends of the sample charging tube 17 respectively. The other two ports of the first three-way connection "a" are connected with one end of the sample needle 7 and one end of the storage tube 8 respectively. The other end of the sample needle 7 extends into the flow chamber 6, and the other end of the storage tube 8 is connected with a port of the injection-suction means 20. The other two ports of the second three-way connection "b" are connected with a sample outlet of the sample pool 5 and a main port of the sample syringe 4 respectively. The conveying line connected between the sample pool 5 and the second three-way connection "b" is provided with a fourth two-way valve V6. In this embodiment, the injection-suction means 20 comprises the sheath liquid syringe 2, the first three-way valve V1 and the second three-way valve V2. The first three-way valve V1 has a normally-closed end which is connected with the storage tube 8, a common end which is connected with the sheath liquid syringe 2, and a normally-opened end which is connected with a common end of the second three-way valve V2. The second three-way valve V2 has, in addition to its common end, a normally-opened end which is connected with the dilution liquid barrel 1, and a normally-closed end which is connected with one end of the first two-way valve V3. The other end of the first two-way valve V3 is connected with the sheath liquid inlet 10 of the flow chamber 6. The sheath liquid syringe 2 is also connected with a side port of the sample syringe 4 via the third two-way valve V5 and the flow restrictor 3. The pressure sensing means 15 is connected to and communicated with the middle way of the conveying line which is connected between the first two-way valve V3 and the sheath liquid inlet 10 of the flow chamber 6. In this embodiment, the pressure sensing means 15 is a pressure sensor. The outlet of the flow chamber 6 is connected with the waste pool 9 via the second two-way valve V4. In this embodiment, a central unit is also provided. The central unit may form a control unit as shown in FIG. 6. The pressure sensor may form a pressure sensing unit as shown in FIG. 6. And the syringes and the valves described above may form a fluid conveying unit as shown in FIG. 6. The central unit controls the opening and closing of the valves and the injection and suction of the syringes according to concrete detection requirements. In particular, when the pressure sensor detected a pressure which is higher than a predetermined upper limit of normal pressure, it reports this condition to the central unit. Then the central unit gives out a command to stop the operation of the corresponding syringe. Thus it can maintain a safety state to avoid any accident. As can be appreciated, the pressure sensor may only report the measured pressure level to the central unit, and the central unit compares the pressure level obtained from the pressure sensor with a predetermined upper limit of normal pressure. If the pressure level is higher than the upper limit, then the central unit gives out a command to stop the operation of the corresponding syringe.

Figure 5:
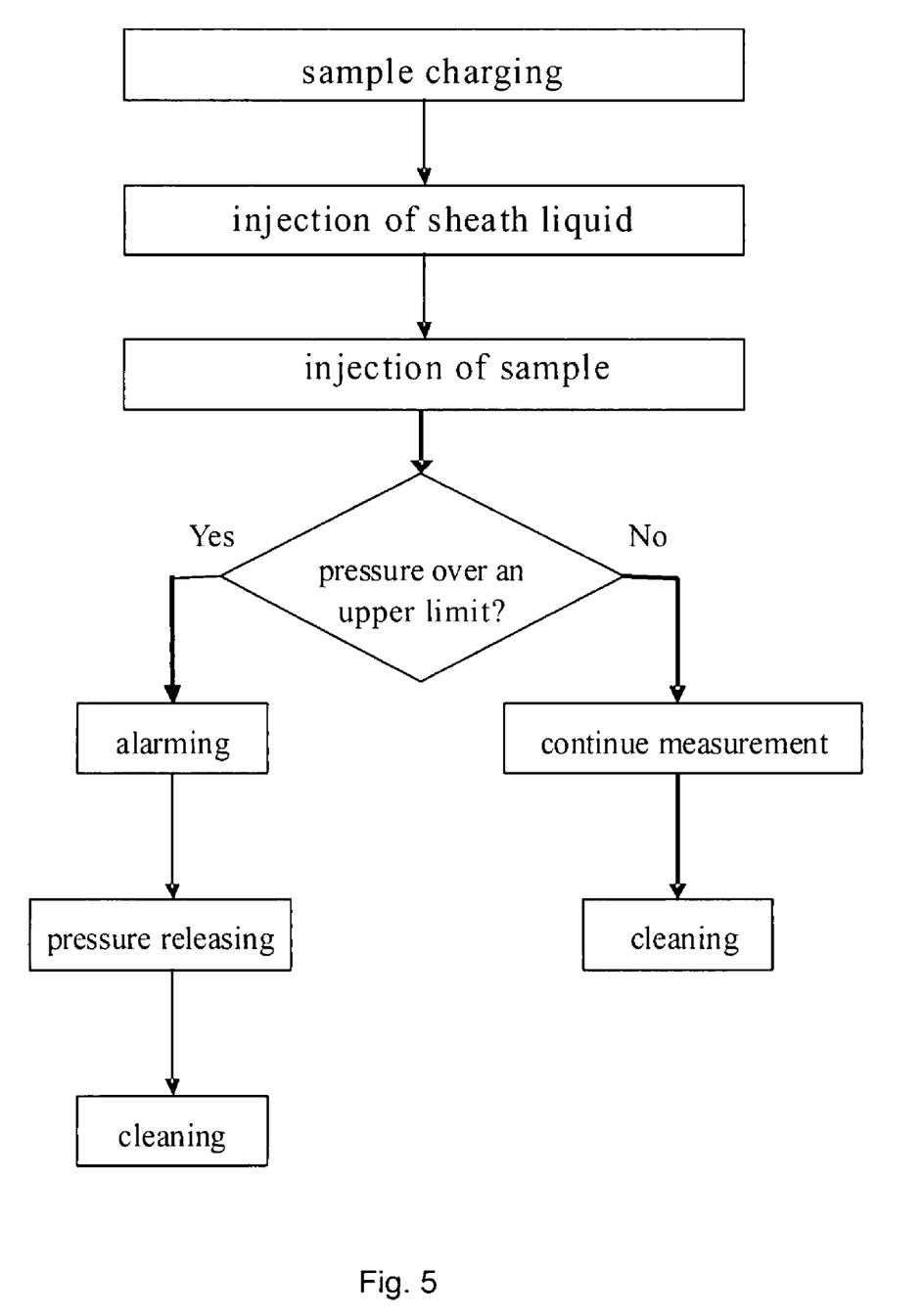
FIG. 5 is a flow chart showing a procedure carried out in an embodiment of the invention.

As shown in FIG. 5, a flow cytometric method performed by the flow cytometric apparatus of the invention comprises the steps discussed below.

First step: sample charging (preloading). The fourth two-way valve V6 is opened, and the first three-way valve V1 is actuated so that its normally-opened end is closed and its normally-closed end is opened. Thus the conveying line connected between the sheath liquid syringe 2 and the sample pool 5 via the sample charging tube 17 is opened to obtain a fluid communication state. The sheath liquid syringe 2 performs suction, so that the sample prepared by reaction is driven from the sample pool 5 into the liquid storage means formed between the storage tube 8 and the fourth two-way valve V6, a metered amount of the sample to be detected is stored in the sample charging tube 17. This process requires that the leading end of the sample should go beyond the first three-way connection "a", but should not go beyond the left end (FIG. 3, the end close to the first three-way valve V1) of the storage tube 8, and the trailing end of the sample should not be left behind the fourth two-way valve V6. In this way, the sample charging tube 17 can be filled up by the sample, while the sample cannot enter into the sheath liquid syringe 2. The sample existed between the first three-way connection "a" and the second three-way connection "b", especially in the sample charging tube 17, is the sample that will be detected afterwards. After the step of sample charging, the fourth two-way valve V6 and the first three-way valve V1 are actuated to return to their normal states.

Second step: injection of sheath liquid. The first two-way valve V3 and the second two-way valve V4 are opened, and the second three-way valve V2 is actuated so that its normally-opened end is closed and its normally-closed end is opened. Thus the conveying line connected between the sheath liquid syringe 2 and the waste pool 9 via the flow chamber 6 is opened to obtain a fluid communication state. The sheath liquid syringe 2 pushes forward the sheath liquid, so as to feed it into the flow chamber 6 to form a sheath flow.

Third step: injection of sample. The sample syringe 4 pushes forward the liquid sample which is previously stored in the sample charging tube 17, so as to feed it into the flow chamber 6. For the purpose of saving time, that is to say, to inject a part of the sample which is proximate to the first three-way connection "a" into the flow chamber 6 quickly, the sample feeding speed of the sample syringe 4 in the initial stage can be high. After the part of sample near the first three-way connection "a" is injected into the flow chamber 6, the sample feeding speed of the sample syringe 4 may be reduced to form a stable and smooth sample flow. Alternatively, before the sample syringe 4 starts to feed the sample, the third two-way valve V5 is opened, and a part of the sample is drawn and branched into a part of the volume of the sheath liquid syringe 2, and the sheath liquid syringe 2 then pushes the sample which is proximate to the first three-way connection "a" into the flow chamber 6 quickly. After the part of sample near the first three-way connection "a" is injected into the flow chamber 6, the sample syringe 4 is opened, and then the third two-way valve V5 is closed, thus a stable and smooth sample flow is formed. In the case that the flow restrictor 3 is a flow restricting tube, the sample flow rate can be adjusted by changing the length of the flow restricting tube.

Fourth step: detection. A detection device is actuated to detect or measure the sample which is passing through the flow chamber in a row in sequence.

Fifth step: cleaning. After detection or measurement, the sample remained in the conveying paths should be cleaned away. To this end, the sample syringe 4 is stopped first. Then the fourth two-way valve V6 is opened, and a part of the sample is drawn into a portion of the volume of the sheath liquid syringe 2. In this way, the sample existed in the sample needle 7 is also drawn back. Then the second two-way valve V4 is closed, and the first three-way valve V1 is actuated so that its normally-opened end is closed and its normally-closed end is opened. The sheath liquid syringe 2 pushes the remaining sample in the conveying line between the storage tube 8 and the fourth two-way valve V6 back into the sample pool 5. Thus this section of conveying line is cleaned.

The above procedure may further comprise the following additional steps.

First additional step: pressure monitoring in sheath-liquid conveying line. During the feeding process of the sheath liquid syringe 2, the pressure sensing means 15 continuously monitors the pressure in the sheath-liquid conveying line. The central unit compares the pressure measured by the pressure sensor 15 with a predetermined upper limit of normal pressure, as shown in FIG. 6. Once the pressure sensing unit, or the pressure sensor, measures a pressure level which is higher than the upper limit of normal pressure, the pressure sensing unit or the pressure sensor reports the abnormal pressure to the central unit or the control unit. The control unit sends out a command to stop the operation of the corresponding syringe in the fluid conveying unit. If the measured pressure level is under the upper limit of normal pressure, then the procedure performs the cleaning step after the detection step, and then it turns to the preparation for the next operation cycle.

Second additional step: cleaning of sheath-liquid conveying line after releasing of overpressure. In this case, after the operation of the corresponding syringe is stopped for the existence of overpressure, corresponding portions of the liquid path should also be cleaned. First, the fourth two-way valve V6 is opened, so that the high pressure in the flow chamber 6 is released. Then the sheath liquid syringe 2 is pushed forward slowly, thus the sheath liquid is fed into the flow chamber 6 via the sheath liquid inlet 10 and forces the sample remained in the sample needle 7 to flow back. Then the first three-way valve V1 is actuated so that its normally-opened end is closed and its normally-closed end is opened, and the sample remained in the conveying line between the fourth two-way valve V6 and the storage tube 8 is pushed back into the sample pool 5 by the sheath liquid syringe 2. Thus this section of conveying line is cleaned.

Second Embodiment of the Invention

Figure 4:
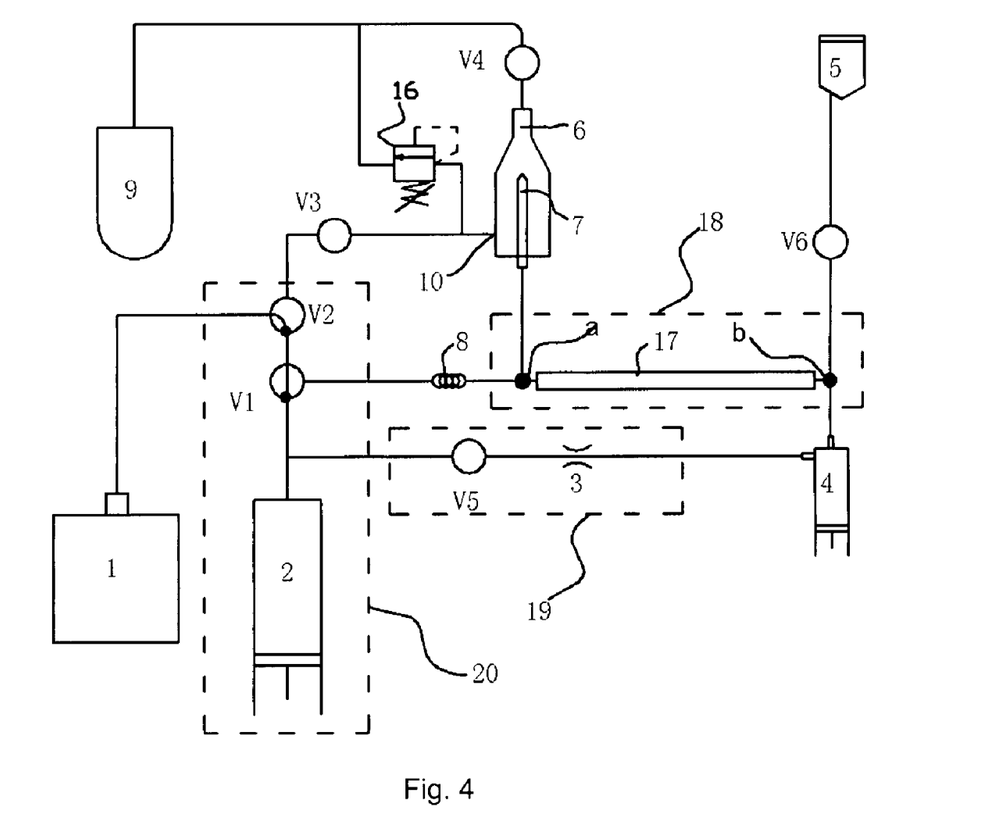
FIG. 4 is a schematic view of the liquid paths in the flow cytometric apparatus according to the second embodiment of the invention in the normal state of the apparatus.

As shown in FIG. 4, the flow cytometric apparatus according to the second embodiment of the invention comprises a dilution liquid barrel 1, a sample syringe 4, a sample pool 5, a flow chamber 6, a sample needle 7, a waste pool 9, a sheath liquid inlet 10, a pressure relieve valve 16, a sample storage means 18, a pressure equalizing means 19, a injection-suction means 20, a first normally-closed two-way valve V3, a second normally-closed two-way valve V4, a fourth normally-closed two-way valve V6 and related conveying lines. The sample storage means 18 comprises a first three-way connection "a", a second three-way connection "b" and the sample charging tube 17. The pressure equalizing means 19 comprises a third normally-closed two-way valve V5 and a flow restrictor 3. The injection-suction means 20 comprises a sheath liquid syringe 2, a first three-way valve V1 and a second three-way valve V2.

As in the first embodiment, the dilution liquid barrel 1 in the second embodiment is designed to store a clean sheath liquid. The sheath liquid syringe 2 is designed to drive the sheath liquid flow from the dilution liquid barrel 1 to the flow chamber 6, and is designed to drive the sample flow from the sample pool 5 to the sample charging tube 17 which is connected with an inlet of the sample needle 7 so that the sample is temporarily stored in a ready to use state. The flow restrictor 3 is designed to restrict the flow rate of the sheath liquid in the pressure equalizing means 19. The flow restrictor 3 may be a flow restricting tube. In this case, the flow rate can be adjusted by changing the length of the flow restricting tube. The sample syringe 4 is designed to push forward the sample to be detected which is stored in the sample charging tube 17, so as to feed it into the flow chamber 6. The sample pool 5 is designed to store the sample to be detected which has been prepared by reaction. The sample surrounded by the sheath liquid passes through the flow chamber 6 and is detected in the meantime. The sample is injected into the flow chamber 6 through the sample needle 7. The sheath liquid syringe 2 functions to provide the flow chamber 6 with a driving power for driving the sheath liquid, and also functions to feed the sample from the sample pool 5 to an inlet of the sample needle 7. The storage tube 8 has a certain volume for storing excessively stored sample, so as to prevent the sample from entering into the sheath liquid syringe 2. The sample charging tube 17 is capable of metering the sample to be detected.

What is different with the first embodiment is that, in the second embodiment, the pressure sensing means 15 of first embodiment is substituted by a pressure relieve valve 16, as shown in FIG. 4. The pressure relieve valve 16 has a function that, when the liquid pressure level received by it is higher than a certain level, it opens a pressure relieve path to ensure that the system is under a safe pressure. As shown in FIG. 4, when the pressure in the sheath-liquid conveying line is over a standard pressure range, the pressure relieve valve 16 is activated, so that the sheath liquid fed by the sheath liquid syringe 2 flows directly to the waste pool 9 via the pressure relieve valve.

The flow cytometric apparatus in the second embodiment of the invention has a liquid path connected in the way discussed below.

As shown in FIG. 4, in this embodiment, the sample storage means 18 comprises the storage tube 8, the sample charging tube 17, the first three-way connection "a" and the second three-way connection "b". The first three-way connection "a" and the second three-way connection "b" each have a port connected with the opposite ends of the sample charging tube 17 respectively. The other two ports of the first three-way connection "a" are connected with one end of the sample needle 7 and one end of the storage tube 8 respectively. The other end of the sample needle 7 extends into the flow chamber 6, and the other end of the storage tube 8 is connected with a port of the injection-suction means 20. The other two ports of the second three-way connection "b" are connected with a sample outlet of the sample pool 5 and a main port of the sample syringe 4 respectively. The conveying line connected between the sample pool 5 and the second three-way connection "b" is provided with a fourth two-way valve V6. In this embodiment, the injection-suction means 20 comprises the sheath liquid syringe 2, the first three-way valve V1 and the second three-way valve V2. The first three-way valve V1 has a normally-closed end which is connected with the storage tube 8, a common end which is connected with the sheath liquid syringe 2, and a normally-opened end which is connected with a common end of the second three-way valve V2. The second three-way valve V2 has, in addition to its common end, a normally-opened end which is connected with the dilution liquid barrel 1, and a normally-closed end which is connected with one end of the first two-way valve V3. The other end of the first two-way valve V3 is connected with the sheath liquid inlet 10 of the flow chamber 6. The sheath liquid syringe 2 is also connected with a side port of the sample syringe 4 via the third two-way valve V5 and the flow restrictor 3. The outlet of the flow chamber 6 is connected with the waste pool 9 via the second two-way valve V4. An overpressure self-release means is connected to and communicated with the middle way of the conveying line which is connected between the first two-way valve V3 and the sheath liquid inlet 10 of the flow chamber 6. In this embodiment, the overpressure self-release means comprises the pressure relieve valve 16. The pressure relieve valve 16 has one end connected with the sheath liquid inlet 10 and another end connected with the waste pool 9.

A flow cytometric method performed by the flow cytometric apparatus of the invention comprises the steps discussed below.

First step: sample charging (preloading). The fourth two-way valve V6 is opened, and the first three-way valve V1 is actuated so that its normally-opened end is closed and its normally-closed end is opened. Thus the conveying line connected between the sheath liquid syringe 2 and the sample pool 5 via the sample charging tube 17 is opened to obtain a fluid communication state. The sheath liquid syringe 2 performs suction, so that the sample prepared by reaction is driven from the sample pool 5 into the liquid storage means formed between the storage tube 8 and the fourth two-way valve V6, a metered amount of the sample to be detected is stored in the sample charging tube 17. This process requires that the leading end of the sample should go beyond the first three-way connection "a", but should not go beyond the left end (FIG. 4, the end close to the first three-way valve V1) of the storage tube 8, and the trailing end of the sample should not be left behind the fourth two-way valve V6. In this way, the sample charging tube 17 can be filled up by the sample, while the sample cannot enter into the sheath liquid syringe 2. The sample existed between the first three-way connection "a" and the second three-way connection "b", especially in the sample charging tube 17, is the sample that will be detected afterwards. After the step of sample charging, the fourth two-way valve V6 and the first three-way valve V1 are actuated to return to their normal states.

Second step: injection of sheath liquid. The first two-way valve V3 and the second two-way valve V4 are opened, and the second three-way valve V2 is actuated so that its normally-opened end is closed and its normally-closed end is opened. Thus the conveying line connected between the sheath liquid syringe 2 and the waste pool 9 via the flow chamber 6 is opened to obtain a fluid communication state. The sheath liquid syringe 2 pushes forward the sheath liquid, so as to feed it into the flow chamber 6 to form a sheath flow.

Third step: injection of sample. The sample syringe 4 pushes forward the liquid sample which is previously stored in the sample charging tube 17, so as to feed it into the flow chamber 6. For the purpose of saving time, that is to say, to inject a part of the sample which is proximate to the first three-way connection "a" into the flow chamber 6 quickly, the sample feeding speed of the sample syringe 4 in the initial stage can be high. After the part of sample near the first three-way connection "a" is injected into the flow chamber 6, the sample feeding speed of the sample syringe 4 may be reduced to form a stable and smooth sample flow. Alternatively, before the sample syringe 4 starts to feed the sample, the third two-way valve V5 is opened, and a part of the sample is drawn and branched into a part of the volume of the sheath liquid syringe 2, and the sheath liquid syringe 2 then pushes the sample which is proximate to the first three-way connection "a" into the flow chamber 6 quickly. After the part of sample near the first three-way connection "a" is injected into the flow chamber 6, the sample syringe 4 is opened, and then the third two-way valve V5 is closed, thus a stable and smooth sample flow is formed. In the case that the flow restrictor 3 is a flow restricting tube, the sample flow rate can be adjusted by changing the length of the flow restricting tube.

Fourth step: detection. A detection device is actuated to detect or measure the sample which is passing through the flow chamber in a row in sequence.

Fifth step: cleaning. After detection or measurement, the sample remained in the conveying paths should be cleaned away. To this end, the sample syringe 4 is stopped first. Then the fourth two-way valve V6 is opened, and a part of the sample is drawn into a portion of the volume of the sheath liquid syringe 2. In this way, the sample existed in the sample needle 7 is also drawn back. Then the second two-way valve V4 is closed, and the first three-way valve V1 is actuated so that its normally-opened end is closed and its normally-closed end is opened. The sheath liquid syringe 2 pushes the remaining sample in the conveying line between the storage tube 8 and the fourth two-way valve V6 back into the sample pool 5. Thus this section of conveying line is cleaned.

The above procedure may further comprise the following additional steps.

First additional step: overpressure protection of sheath-liquid conveying line. As shown in FIG. 4, during the feeding process of the sheath liquid syringe 2, when the pressure in the sheath-liquid conveying line is over a standard range. The overpressure self-release means is activated, so that the sample pushed forward by the sheath liquid syringe 2 flows directly to the waste pool 9 via the overpressure self-release means to ensure that the system is under a safe pressure.

Second additional step: cleaning of sheath-liquid conveying line after releasing of overpressure. In this case, after the operation of the syringe is stopped for the existence of overpressure, corresponding portions of the liquid path should also be cleaned. First, the fourth two-way valve V6 is opened, so that the high pressure in the flow chamber 6 is released. Then the sheath liquid syringe 2 is pushed forward slowly, thus the sheath liquid is fed into the flow chamber 6 via the sheath liquid inlet 10 and forces the sample remained in the sample needle 7 to flow back. Then the first three-way valve V1 is actuated so that its normally-opened end is closed and its normally-closed end is opened, and the sample remained in the conveying line between the fourth two-way valve V6 and the storage tube 8 is pushed back into the sample pool 5 by the sheath liquid syringe 2. Thus this section of conveying line is cleaned.

The flow cytometric apparatus and method of the present invention are particularly applicable in the fields of blood cell detection and particle analysis, for detecting or measuring the number and size of cells or particles. However, the flow cytometric apparatus and method of the present invention can also be used in various other detection and analysis fields.

The present invention is described with reference to its preferred embodiments which are not intended to restrict the scope of the present invention. A skilled in the art will readily recognize that modifications and changes can be made to the embodiments without departing from the spirit of the present invention, and accordingly all these modifications and changes may be regarded as falling within the scope of the present invention.

What are claimed are:

1. A flow cytometric apparatus comprising:
   a flow chamber adapted to be passed through by a sample to be detected in a row in sequence so that the sample can be detected, the flow chamber comprising a sheath liquid inlet for the injection of a sheath liquid and a sample needle for the injection of the sample;
   a sample storage means for storing the sample to be detected;

a sample syringe for driving the sample to be detected into the flow chamber, so as to form a sample flow to be detected;

a syringe-type injection-suction means comprising a sheath liquid syringe and a liquid-path switching means connected with it, wherein the liquid-path switching means controllably connects the sheath liquid inlet and the sample storage means for receiving the sheath liquid, and wherein the injection-suction means functions in a manner that, in a sample charging stage, the injection-suction means feeds the sample into the sample storage means so that the sample is temporarily stored in it in a ready-to-use state, and in a sheath-liquid injection stage, the injection-suction means feeds the sheath liquid into the flow chamber to form a sheath flow; and a control unit for controlling the operations of the sample syringe and the syringe-type the injection-suction means.

2. The flow cytometric apparatus of claim 1, wherein when the sheath liquid syringe is actuated for suction, the sample is fed into the liquid storage means, or the sheath liquid is drawn into the sheath liquid syringe, and when the sheath liquid syringe is actuated for injection, the sheath liquid is fed into the flow chamber through the sheath liquid inlet to form the sheath flow.

3. The flow cytometric apparatus of claim 2, wherein the liquid-path switching means comprises a first three-way valve and a second three-way valve, the first three-way valve having a common end which is connected with the sheath liquid syringe, a normally-closed end which is connected with the sample storage means, and a normally-opened end which is connected with a common end of the second three-way valve, and the second three-way valve having the common end which is connected with the normally-opened end of the first three-way valve, a normally-opened end which is connected for receiving the sheath liquid, and a normally-closed end is connected with the sheath liquid inlet.

4. The flow cytometric apparatus of claim 2, further comprising an overpressure protection means which is connected to and communicated with a conveying line provided between the sheath liquid inlet and the injection-suction means.

5. The flow cytometric apparatus of claim 4, wherein the overpressure protection means comprises a pressure sensing means which is connected to and communicated with a conveying line provided between the injection-suction means and the sheath liquid inlet, for monitoring the pressure in the sheath-liquid conveying line, and wherein the pressure sensing means is connected with the control unit, and the control unit compares the pressure level obtained from the pressure sensing means with a predetermined upper limit of normal pressure and sends out a command to stop the operation of a corresponding syringe when the pressure level is determined to be an overpressure.

6. The flow cytometric apparatus of claim 5, wherein the pressure sensing means is a pressure sensor.

7. The flow cytometric apparatus of claim 4, wherein the overpressure protection means is an overpressure self-release means, the overpressure self-release means having one end connected with a conveying line provided between the sheath liquid inlet and the injection-suction means and another end connected with a waste pool.

8. The flow cytometric apparatus of claim 7, wherein the overpressure self-release means is a pressure relieve valve.

9. The flow cytometric apparatus of claim 1, wherein the liquid storage means comprises a sample charging tube, a first three-way connection and a second three-way connection, the sample charging tube having one end connected with the sample needle and the injection-suction means via the first, three-way connection and another end connected with the sample syringe via the second three-way connection.

10. The flow cytometric apparatus of claim 9, further comprising a storage tube which is connected between the injection-suction means and the first three-way connection.

11. The flow cytometric apparatus of claim 1, further comprising a pressure equalizing means which is connected between the injection-suction means and the sample syringe, wherein, before the sample syringe is actuated for feeding the sample, the sample flows into the flow chamber quickly by the activation of the pressure equalizing means.

12. The flow cytometric apparatus of claim 11, wherein the pressure equalizing means comprises a third two-way valve and a flow restrictor, the flow restrictor having one end connected with the sample syringe and another end connected with the injection-suction means via the third two-way valve.

13. A flow cytometric method performed by the flow cytometric apparatus of claim 1, comprising the steps of:
  A) sample charging, in which, by means of the injection-suction means, the sample to be detected is fed into the sample storage means so that the sample is temporarily stored in it in a ready-to-use state;
  B) injection of the sheath liquid, in which, by means of the injection-suction means, the sheath liquid is injected into the flow chamber to form a stable and smooth sheath flow;
  C) injection of sample, in which the sample to be detected, which is stored in the sample storage means, is injected into the flow chamber to form a stable and smooth sample flow to be detected; and
  D) detection, in which the sample flow passing through the flow chamber is detected.

14. The flow cytometric method of claim 13, wherein when the sheath liquid is injected, an overpressure protection means is activated to perform overpressure protection in the sheath-liquid conveying line.

15. The flow cytometric method of claim 14, wherein the overpressure protection means is a pressure sensing protection means which monitors the pressure in the sheath-liquid conveying line by a pressure sensing means, and the control unit compares the pressure level obtained from the pressure sensing means with a predetermined upper limit of normal pressure and sends out a command to stop the operation of a corresponding syringe when the pressure level is determined to be an overpressure.

16. The flow cytometric method of claim 14, wherein the overpressure protection means is an overpressure self-release means, and when the pressure in the sheath-liquid conveying line is at an overpressure, the overpressure self-release means bypasses the sheath flow around the flow chamber, so that the sheath is drained directly into a waste pool via the flow overpressure self-release means.

17. The flow cytometric method of claim 15, further comprising a step of cleaning of sheath-liquid conveying line after releasing of overpressure, in which, after the operation of the syringe is stopped in an overpressure condition and the overpressure in the flow chamber is released, the parts of the conveying line which have been flowed through by the sample flow are cleaned by a flow of sheath liquid.

18. The flow cytometric method of claim 17, wherein the step of cleaning of sheath-liquid conveying line after releasing of overpressure is a back flow cleaning step, in which the washing sheath liquid flows in a direction reverse to that of the sample, so that the sample remained in the conveying line is forced back to the sample pool.

19. The flow cytometric method of claim 13, further comprising a step of cleaning, in which, after detection, the sheath liquid washes the parts of the conveying line which have been flowed through by the sample flow.

20. The flow cytometric method of claim 13, further comprising a step of pressure equalizing, in which, before the sample is injected, a the pressure equalizing means is activated, so that a part of the sample to be detected, which is stored in the sample storage means, is branched out from the sample storage means and is then injected into the flow chamber quickly.

* * * * *